United States Patent [19]

Garlisi et al.

[11] Patent Number: 4,797,481

[45] Date of Patent: Jan. 10, 1989

[54] SURFACTANTS DERIVED FROM DI- OR TRI-CARBOXYLIC HYDROXY-ACIDS

[75] Inventors: Salvatore Garlisi, Vercelli; Luigi Turchini, Milan; Aurelio Albanini, Casteggio; Dario Fornara, Massiola, all of Italy

[73] Assignee: Raffineria Olii Lubrificanti "R.O.L." S.p.A., Milan, Italy

[21] Appl. No.: 88,382

[22] Filed: Aug. 24, 1987

[30] Foreign Application Priority Data

Aug. 28, 1986 [IT] Italy ................................ 21540 A/86

[51] Int. Cl.$^4$ ............ C07H 15/04; C07H 13/02; C07H 15/00; B01F 17/00

[52] U.S. Cl. ........................ 536/116; 536/18.2; 536/119; 536/1.1; 252/174.17; 252/174.18; 252/174.19; 252/DIG. 1

[58] Field of Search ............ 252/174.17, 174.18, 252/174.19, DIG. 1; 536/18.2, 116, 119, 1.1; 514/23

[56] References Cited

U.S. PATENT DOCUMENTS

| | | |
|---|---|---|
| 2,927,919 | 3/1960 | Anderson ............... 536/116 |
| 2,938,027 | 5/1960 | Gladstone .............. 536/116 |
| 3,872,020 | 3/1975 | Yamagishi et al. ...... 252/174.19 |
| 3,940,424 | 2/1976 | Lannert ............... 252/174.19 |
| 4,137,401 | 1/1979 | Lemieux et al. ........ 536/116 |
| 4,215,213 | 7/1980 | Inoue et al. .......... 536/116 |
| 4,259,202 | 3/1981 | Tanaka et al. ......... 252/174.18 |
| 4,268,498 | 5/1981 | Gedeon et al. ........ 536/119 |
| 4,665,057 | 5/1987 | Nelson et al. ........ 514/23 |

FOREIGN PATENT DOCUMENTS 06236 10/1987 World Int. Prop. O.

*Primary Examiner*—Paul Lieberman
*Assistant Examiner*—Ronald A. Krasnov
*Attorney, Agent, or Firm*—Stevens, Davis, Miller & Mosher

[57] ABSTRACT

Surfactants consisting of esters of di- or tri-carboxylic hydroxyacids having the formula:

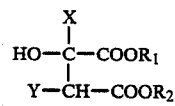

wherein:
  X=H, —CH$_2$COOR;
  Y=H, OH, with the proviso that Y=H when X=—CH$_2$COOR;
  R, R$_1$, R$_2$, which may be the same or different, are H an alkali or alkaline-earth metal, —NH$_4$, a cation of an ammonium organic base, or an A radical selected from the group consisting of etherified (C$_6$–C$_{16}$) alkyl polysaccharides containing from 2 to 6 saccharide units and etherified (C$_6$–C$_{16}$) hydroxyalkyl aliphatic polyalcohols containing from 2 to 16 hydroxyl groups;

and wherein at least one of said R, R$_1$, R$_2$ is an A radical.

11 Claims, No Drawings

SURFACTANTS DERIVED FROM DI- OR TRI-CARBOXYLIC HYDROXY-ACIDS

DESCRIPTION OF THE INVENTION

The present invention relates to surfactants derived from di- or tri-carboxylic hydroxyacids with polyhydroxylated compounds.

In many classes of known surfactants it is difficult to find a group of characteristics all present in a single product, such as biodegradability, non-toxicity, lack of irritant effects on the skin, a high water solubility, in addition to excellent detergent properties, that would make such a product particularly versatile and therefore make it utilizable equally for the most diverse uses such as, for instance, detergency in general, the toilette field, beauty culture, the foodstuff industry, the textile industry, emulsion polymerization, etc.

We have now found surfactants derived from di- or tri-carboxylic hydroxyacids, more particularly consisting of esters of citric, tartaric or malic acid, with alkyl ethers of polysaccharides or with hydroxyalkylethers of polyalcohols, as well as of salts thereof with inorganic or organic bases, which surfactants have, in combination, the aforesaid good characteristics and which therefore have proved to be suitable for a great many applications.

Therefore the present invention relates to esters of di-or tri-carboxylic hydroxyacids having the formula:

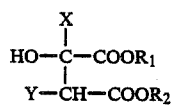

(I)

wherein:

X is H or a —CH$_2$COOR group;

Y is H or —OH, with the proviso that Y is H when X is —CH$_2$COOR;

R, R$_1$, R$_2$, which may be the same or different, represent a hydrogen atom, an alkali or alkaline-earth metal, an ammonium group, the cation of an ammonium organic base, or an A radical derived from a polyhydroxylated organic compound selected from the group consisting of etherified (C$_6$–C$_{16}$) alkyl polysaccharides containing from 2 to 6 monoeric saccharide units and etherified (C$_6$–C$_{16}$) hydroxyalkyl aliphatic polyalcohols containing from 2 to 16 hydroxyl radicals, with the proviso that at least one of said R, R$_1$, R$_2$ is an A radical and wherein a hydroxyl radical or hydroxyl radicals of the acid group of the ethers having formula (I) may be optionally esterified or etherified by the usual methods.

The alkali metal is preferably sodium or potassium and the alkaline-earth metal is preferably magnesium.

The cation of an ammonium organic base may come, for instance, from an alkanolamine such as monoethanolamine or triethanolamine.

As A radicals derived from etherified (C$_6$–C$_{16}$) alkyl polysaccharides, use may be made, for instance, of those derived from monoalkyletherified polyglucose having the formula:

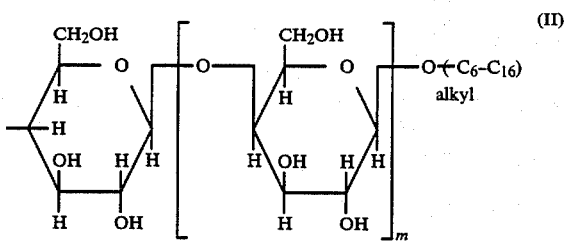

(II)

wherein m is a whole number ranging from 1 to 5.

As A radicals derived from etherified (C$_6$–C$_{16}$) hydroxyalkyl aliphatic polyalcohols, use may be made, for instance of those having the formula:

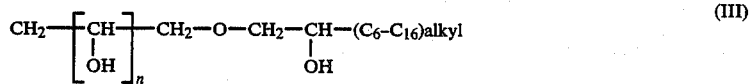

(III)

wherein n is a whole number ranging from 1 to 15;

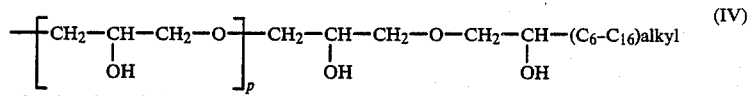

(IV)

wherein p is a whole number ranging from 1 to 10;

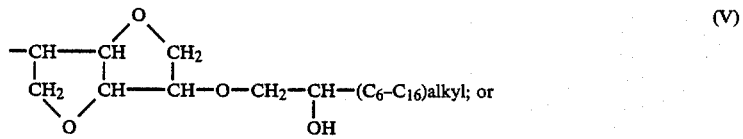

(V)

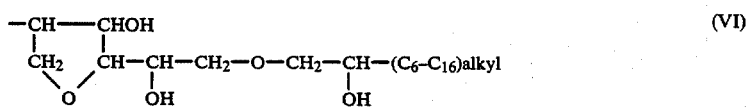

(VI)

Esters having the formula (I) are prepared according to a particular process, and this forms a further aspect of the present invention, comprising esterification of citric, tartaric or malic acid with a polyhydroxylated organic compound having the formula

(VII)

wherein A has the aforesaid meaning, by heating at a temperature of 120°–140° C., with continuous distillation of the water forming during the reaction and, optionally, final salification of the obtained product by means of bases of alkali or alkaline-earth metals, ammonia or amines. As base, use may be made, for instance, of sodium, potassium, magnesium, or ammonium hydroxide, triethanolamine or monoethanolamine.

By the aforesaid process, starting from citric acid, one obtains mono, di- and tri-esters having the following formulae respectively:

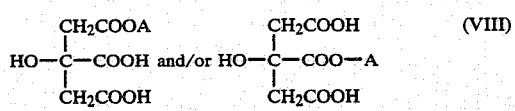
(VIII)

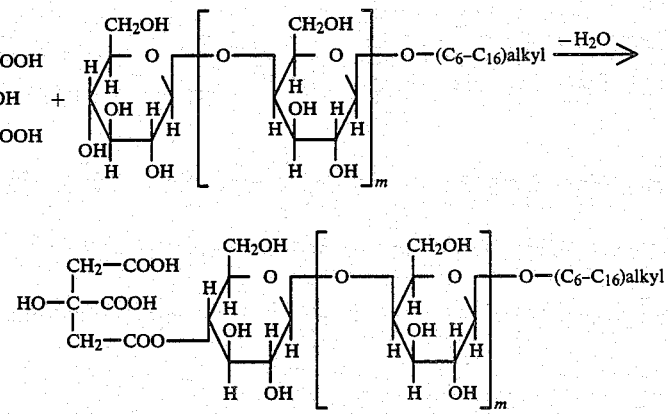
(IX)

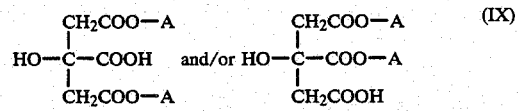
(X)

Starting from tartaric acid, one obtains mono- and di-esters having the following formulae respectively:

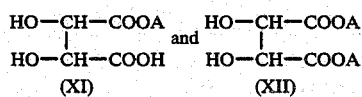
(XI) (XII)

Starting from malic acid, one obtains mono- and di-esters having the following formulae respectively:

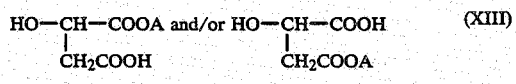
(XIII)

(XIV)

According to the reaction conditions employed, and according to the molar ratios hydroxyacid/polyhydroxylated compound, it is possible to prepare selectively mono-, di- and in the case of citric acid, tri-ester as well.

Thus hydroxyacid and polyhydroxylated compound (VII) are reacted in substantially equimolecular ratios in order to produce preferably mono-esters having formula (VIII), (XI) and (XIII).

In the case of the preparation of citric mono-ester of monoalkyl etherified polyglucose, the reaction may be represented according to the following equation:

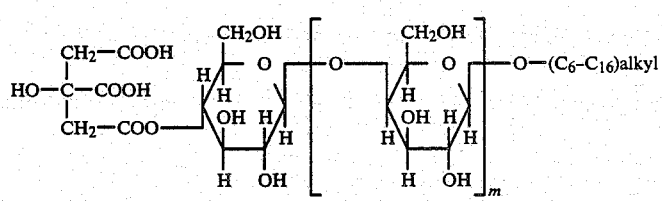

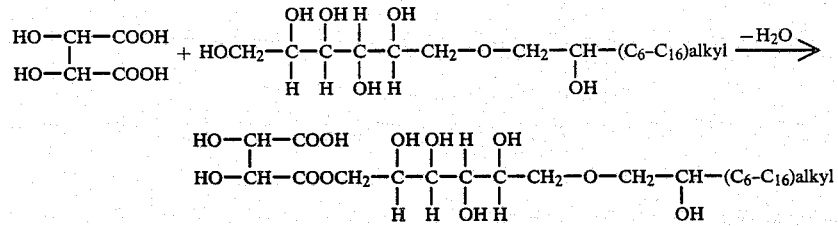

In the case of the preparation of tartartic mono-ester of monohydroxyalkyletherified sorbitol, the reaction may be represented according to the following equation:

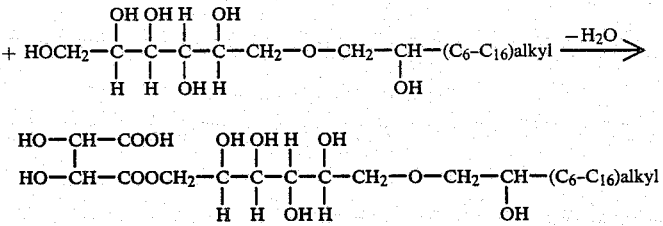

The polyhydroxylated organic compounds having formula (VII), such as alkyletherified polysaccharides and hydroxyalkyletherified polyalcohols, are known products or may be prepared by known methods; sometimes they may be found on the market.

In particular, the monoalkyletherified polysaccharides may be prepared by etherification of the polysaccharide with ($C_6$-$C_{16}$) fatty alcohols.

The monohydroxyalkyletherified polyalcohols may be prepared by reaction of the polyalcohol with a ($C_6$-$C_{16}$) alkyl α-epoxide.

Among the alkyletherified polysaccharides, preference is given to polyglucose monoalkyletherified with octylic and decylic alcohols.

Among the hydroxyalkyletherified polyalcohols, preference is given to sorbitol monohydroxyalkyletherified with octene-1-oxide and/or decene-1-oxide.

The esters according to the present invention, and in particular the mono-esters of alkyletherified polysaccharides or of hydroxyalkyletherified polyalcohols, salts and mixtures thereof, are very efficient surfactants, allowing, even when employed in very low percentages, a remarkable lowering of the surface tension and therefore they may be used as emulsifiers, dispersing agents, or detergents in general.

Besides their excellent detergent properties, they do not present any toxic effect, as well as any irritant effect on skin and eyes, and they do not present any acute toxicity if they are swallowed orally.

They are highly biodegradable, showing biodegradability values over 90%.

They prove to be stable within a wide range of temperatures up to 100° C. and after a storage at low temperatures for a long time, and when they are brought to room temperature they do not give rise to any separation.

They show a good but not excessive wetting power and a good foam-forming power. They may have from a moderate to an excellent water solubility.

In particular, their solubility increases by increasing the number of hydroxyl radicals of the polyhydroxylic part of the alkyletherified or hydroxyalkyletherified compound.

The esters, according to the present invention, have proved to be compatible with most of the known surfactants and therefore they may be formulated with them.

The esters according to this invention, on account of their entire panoply of characteristics, have proved to be very flexible as to their different applications of surface-active agents.

On account of their high detergent power joined to their lack of toxic effects on the skin, hair, eyes, these esters are particularly suitable for applications in the beauty culture field such as, for instance, for the preparation of liquid or creamy detergents for the skin, shampoos, bath foams, etc.

The following examples will illustrate the invention, without limiting, however, the scope.

EXAMPLE 1

Preparation of esters of citric acid by polyglucose monoalkylethers.

Esterification 144.0 g (0.75 moles) of anhydrous citric acid and 784.9 g (0.75 moles) of TRITON-CG/110$^R$ at 60% in water were fed, under nitrogen flow, into a reactor equipped with a heating system, stirrer, vacuum pipe connection, thermometer, system for feeding the reactants, and connected to a cooler equipped with a manifold for collecting the dilution water and subsequently the reaction water.

Vacuum was produced inside the apparatus by means of a water pump, and while keeping the mixture under stirring, the temperature was brought to 90°–105° C. in about 40 minutes, in order to remove the dilution water afterwards, the vacuum was stopped and the temperature was bought to 124°–125° C. under nitrogen flow; the reaction mixture was kept at that temperature over a period of about 100 minutes, until the acid value was 145±3.

The mixture was cooled to a temperature of 110°–115° C., diluted with about 300 g. of water equal to 50% of the calculated amount of acid monoester, cooled to 50° C., and finally the reactor was unloaded.

One thus obtained 900 g of a limpid liquid product containing 33.33% of water, having an acid value of 97.4, a saponification number of 140, and consisting substantially of citric acid monoester.

TRICON-CG/110$^R$ consisted of a mixture of polyglucose monoalkylethers at 60% in water of the formula:

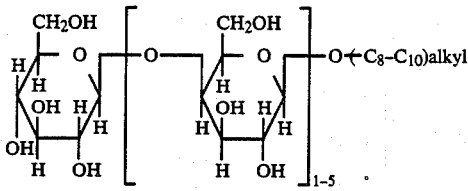

having a hydroxyl number of 879.9, determined on the dry product, obtained by etherification of polyglucose containing from 2 to 6 glucose units with a mixture 50/50 of octylic and decylic alcohol.

Salification 339.6 g of the citric monoester at 66.66% in water, prepared in advance, and 581.7 g of demineralized water were fed into a vessel equipped with a stirrer, thermometer, dropping funnel, and water cooling system.

The mixture was stirred until a limpid solution was obtained; afterwards, under stirring, 78.7 g of an aqueous solution of NaOH at 30% were fed slowly, in about 1 hour, through a dropping funnel, while keeping the temperature at values below 30° C.

One thus obtained 1000 g of a limpid aqueous solution containing 25% by weight of citric monoester salified with sodium.

The solution thus obtained may be employed, either as such or after having been diluted, for the different uses of detergency.

A completely viscous limpid liquid was obtained from the solution, after having removed the water by heating at 50° C. over 16 hours under vacuum; such a liquid consisted prevailingly of the sodium salt of citric monoester, having an acid value of 5, a saponification number of 71.0, an esterification number of 66.0, and a pH value of 6.8 at 1%.

The salified product proved to be perfectly soluble in water in any ratio, yielding limpid soslutions at 25° C. up to a concentration of 25%, and more or less viscous solutions at higher concentrations.

Moreover, the following tests were carried out on the salified product:

Surface tension

The surface tension, measured at 20° C. according to the DU NOUY method, was 42.0 dynes/cm at a concentration of 0.25 g/l, and 32.3 dynes/cm at a concentration of 1 g/l.

Imbibition power

The imbibition power, determined on the product at a concentration of 2 g/l in distilled water, was over 1800 seconds.

Foam-forming power

This was determined on 200 ml of an aqueous solution containing 2 g/l of the product, by using a bored flat piston system, 50 strokes. The following results were obtained:

| After minutes | foam ml |
| --- | --- |
| 0 | 790 |
| 5 | 780 |
| 10 | 770 |

-continued

| After minutes | foam ml |
| --- | --- |
| 15 | 770 |
| 20 | 770 |
| 25 | 760 |
| 30 | 760 |

Moreover, the salified product proved to be highly biodegradable, non-toxic, non-irritating, and endowed with an excellent detergent power.

EXAMPLE 2

75.1 g (0.5 moles) of anhydrous tartaric acid and 523.2 g (0.5 moles) of TRITON-CG/110$^R$ at 60% in water were fed, under nitrogen flow, into a reactor equipped with a heating system, stirrer, vacuum pipe connection, thermometer, system for feeding the reactants, and connected to a cooler equipped with a manifold for collecting the dilution water and subsequently the reaction water.

Vacuum was produced inside the apparatus by means of a water pump, and while keeping the mixture under stirring, the temperature was brought to 90°-105° C. in about 50 minutes, in order to remove the dilution water; afterwards, the vacuum was stopped and the temperature was brought to 118°-120° C. under nitrogen flow; the reaction mixture was kept at that temperature over about 90 minutes, until the acid value was 85±3.

The mixture was cooled to a temperature of 110°-115° C., diluted with about 188 g of water, equal to 50% of the calculated amount of acid monester, cooled to about 50° C., and finally the reactor was unloaded.

One thus obtained 564 g of a limpid liquid product, containing 33.33% of water, having an acid value of 50.0, a saponification number of 98.4, and consisting substantially of the tartaric acid monoester.

Salification 356.1 g of the tartaric monoester at 66.66% in water, prepared in advance, and 601.5 g of demineralized water were fed into a vessel equipped with a stirrer, thermometer, dropping funnel, and water cooling system.

The mixture was stirred until a limpid solution was obtained; afterwards, under stirring, 42.4 g of an aqueous solution of NaOH at 30% were fed slowly in about 1 hour, through a dropping funnel, while keeping the temperature at values below 30° C.

One thus obtained 1000 g of a limpid aqueous solution containing 25% by weight of tartaric monoester, salified with sodium.

The solution thus obtained may be employed, either as such or after having been diluted, for the different uses of detergency.

A completely viscous limpid liquid was obtained from the solution, after having removed the water by heating at 50° C. over 16 hours under vacuum; such a liquid consisted prevailingly of the sodium salt of tartaric monoester, having an acid value of 2.4, a saponification number of 77.2, an esterification number of 74.8, and a pH value of 6.8 at 1%.

The salified product proved to be perfectly soluble in water in any ratio, yielding limpid solutions at 25° C. up to a concentration of 25%, and more or less viscous solutions at higher concentrations.

Moreover, the following tests were carried out on the salified product;

Surface tension

The surface tension, measured at 20° C. according to the DU NOUY method, was 43.5 dynes/cm at a concentration of 0.25 g/l, and 30.0 dynes/cm at a concentration of 1 g/l.

Imbibition power

The imbibition power, determined on the product at a concentration of 2 g/l in distilled water, was over 1800 seconds.

Foam-forming power

This was determined on 200 ml of an aqueous solution containing 2 g of the product, by using a bored flat piston system, 50 strokes. The following results were obtained:

| After minutes | foam ml |
| --- | --- |
| 0 | 790 |
| 5 | 780 |
| 10 | 780 |
| 15 | 780 |
| 20 | 770 |
| 25 | 770 |
| 30 | 760 |

Moreover the salified product proved to be highly biodegradeable, non-toxic, non-irritating, and endowed with an excellent detergent power.

EXAMPLE 3

Preparation of monoester of citric acid by sorbitol 2-hydroxyoctyl-ether.

Esterification 126.7 g (0.66 moles) of anhydrous citric acid and 200.0 g (0.66 moles) of sorbitol 2-hydroxyoctyl-ether were fed, under nitrogen flow, into a reactor equipped with a heating system, stirrer, thermometer, system for feeding the reactants, and connected to a cooler equipped with a manifold for collecting the reaction water.

The temperature was brought, under stirring and nitrogen flow, to 140°-142° C. in about 90 minutes, and the reaction mixture was kept at that temperature for about 50 minutes, until the acid value was 240±5.

The mixture was cooled to a temperature of 110°-115° C., diluted with about 157 g of water, equal to 50% of the calculated amount of acid monoester, cooled to 50° C. and finally the reactor was unloaded.

One thus obtained 471 g of a viscous liquid containing 33.33% of water having an acid value of 156.8, a saponification number of 235.2, and consisting substantially of citric acid monoester.

Sorbitol 2-hydroxyoctyl-ether having the formula:

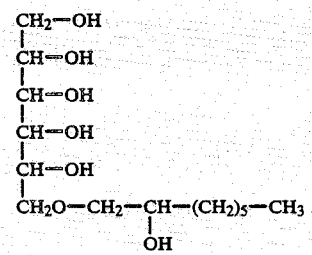

having a hydroxyl number of 1111.0 and a molecular weight of 303, was similarly obtained, by reacting sorbitol with octene-1-oxide.

Salification 321.2 g of the citric monoester at 66.66% in water, prepared in advance, and 559.2 g of demineralized water were fed into a vessel equipped with a stirrer, thermometer, dropping funnel, and a water cooling system.

The mixture was stirred until a homogeneous emulsion was obtained; afterwards under stirring, 119.6 g of an aqueous solution of NaOH at 30% were fed slowly in about 1 hour through a dropping funnel, while keeping the temperature at values below 30° C.

1000 g of a slightly cloudy aqueous solution were obtained. Then by paper filtration one obtained a limpid aqueous solution containing 25% by weight of citric monoester salified with sodium.

The solution thus obtained may be used either as such or after having been diluted, for the different uses of detergency.

A completely viscous limpid liquid was obtained from the solution, after having removed the water by heating at 50° C. over 16 hours under vacuum; such a liquid consisted prevailingly of the sodium salt of citric monoester, having an acid value of 4.5, a saponification number of 119.4, an esterification number of 114.9, and a pH value of 6.8 at 1%.

The salified product proved to be perfectly soluble in water in any ratio, yielding limpid solutions at 25° C. up to a concentration of 25%, and more or less viscous solutions at higher concentrations.

The following tests were carried out on the salified product:

Surface tension

The surface tension, measured at 20° C. according to the DU NOUY method, was 29.5 dynes/cm at a concentration of 0.25 g/l, and 27.5 dynes/cm at a concentration of 1 g/l Imbibition power The imbibition power, determined on the product at a concentration of 2 g/l in distilled water, was over 1800 seconds.

Foam-forming power

This was determined on 200 ml of an aqueous solution containing 2 g/l of the product, by using a bored flat piston system, 50 strokes. The following results were obtained:

| After minutes | foam ml |
|---|---|
| 0 | 530 |
| 5 | 530 |
| 10 | 520 |
| 15 | 510 |
| 20 | 480 |
| 25 | 450 |
| 30 | 410 |

Moreover the salified product proved to be highly biodegradable, non-toxic, non-irritating, and endowed with an excellent detergent power.

What is claimed:

1. Esters of di- or tri-carboxylic hydroxyacids having the formula:

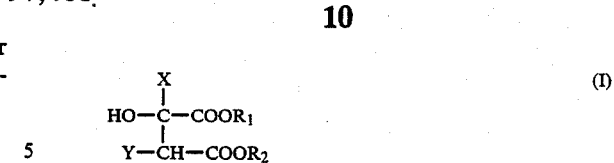

wherein:
X is H or a —CH$_2$COOR group;
Y is H or —OH, with the proviso that Y is H when X is —CH$_2$COOR;
R, R$_1$, R$_2$, which may be the same or different, represent a hydrogen atom, an alkali or alkaline-earth metal, an ammonium group, the cation of an ammonium organic base, or an A radical derived from a polyhydroxylated organic compound selected from the group consisting of etherified (C$_6$–C$_{16}$) alkyl polysaccharides containing from 2 to 6 monomeric saccharide units and etherified (C$_6$–C$_{16}$) hydroxyalkyl aliphatic polyalcohols containing from 2 to 16 hydroxyl radicals, with the proviso that at least one of said R, R$_1$, R$_2$ is an A radical.

2. Esters, according to claim 1, wherein the A radical is selected from the group consisting of polyglucose (C$_6$–C$_{16}$) monoalkyl ethers containing from 2 to 6 glucose units and sorbitol (C$_6$–C$_{16}$) monohydroxyalkyl ethers.

3. Esters according to claim 1, wherein the hydroxyl radical or the hydroxyl radicals of the acid group of the esters having formula (I) are esterified or etherified.

4. Citric acid monoesters according to claim 1, with polyglucose (C$_8$–C$_{10}$) monoalkylethers containing from 2 to 6 glucose units or salts thereof with inorganic or organic bases.

5. Citric acid monoesters according to claim 1, with sorbitol 2-hydroxyoctylether or salts thereof with inorganic or organic bases.

6. Tartaric acid monoesters according to claim 1, with polyglucose (C$_8$–C$_{10}$) monoalkyl ethers containing from 2 to 6 glucose units or salts thereof with inorganic or organic bases.

7. A tartaric acid monoester according to claim 1, with sorbitol 2-hydroxy octylether or salts thereof with inorganic or organic bases.

8. A process for preparing esters having the formula (I) according to claim 1, consisting essentially of esterifying citric, tartaric or malic acid with a polyhydroxylated compound having the formula:

A-OH (VII)

wherein A has the meaning according to claim 1, by heating at a temperature of 120°–140° C., with continuous distillation of the water forming during the reaction and optionally salification of the obtained product with a base of an alkali or alkaline-earth metal, ammonia or an amine.

9. A process according to claim 8, wherein the A radical is selected from the group consisting of polyglucose (C$_6$–C$_{16}$) monoalkyl ethers containing from 2 to 6 glucose units and sorbitol (C$_6$–C$_{16}$) monohydroxyalkyl ethers.

10. Cosmetic and detergent compositions containing one or more esters according to any one of claims 1 to 7.

11. Surface-active agents comprising one or more esters according to any one of claims 1 to 7.

* * * * *